US006565870B1

(12) United States Patent
Donovan

(10) Patent No.: US 6,565,870 B1
(45) Date of Patent: May 20, 2003

(54) METHODS FOR TREATING BONE TUMORS

(75) Inventor: Stephen Donovan, Capistrano Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 09/561,106

(22) Filed: Apr. 28, 2000

(65) Prior Publication Data

(65)

(51) Int. Cl.$^7$ ................................................. A61K 9/00
(52) U.S. Cl. ...................................................... 424/423
(58) Field of Search .............................. 514/2, 14, 825, 514/885; 424/282.1, 247.1, 810, 236.1, 239.1, 423

(56) References Cited

U.S. PATENT DOCUMENTS

| | | | |
|---|---|---|---|
| 5,437,291 A | | 8/1995 | Pasricha et al. |
| 5,714,468 A | | 2/1998 | Binder |
| 5,721,215 A | | 2/1998 | Aoki et al. |
| 5,766,605 A | | 6/1998 | Sanders et al. |
| 5,837,265 A | * | 11/1998 | Montal et al. |
| 6,046,178 A | * | 4/2000 | Silvetti |
| 6,063,768 A | * | 5/2000 | First .............................. 514/14 |
| 6,113,915 A | * | 9/2000 | Aoki et al. |
| 6,139,845 A | | 10/2000 | Donovan |

FOREIGN PATENT DOCUMENTS

| | | |
|---|---|---|
| WO | WO94/15629 | 7/1994 |
| WO | WO94/21300 | 9/1994 |
| WO | WO95/17904 | 7/1995 |
| WO | WO96/33273 | 10/1996 |

OTHER PUBLICATIONS

Okada et al., "Prevention of Lung Metastasis by Intra–tumoral Injection of Cepharanthin and Staphylococcal Enterotoxin B in Transplantable Rat Osteosarcoma", Jpn. J. Cancer Res 90, 928–933, Sep. 1999.*

Nilsonne U, "Treatment of osteosarcoma by interferon and differentiated surgery", Sem Hop 1982 Sep. 2; 58 (30–31): 1764–6.*

Kisenishsky et al., "Effect of AF64A on Cerebral Oxygen Consumption in Young and Old Rats", Neurobiol Aging 1987 Mar.–Apr.; 8(2):139–45.*

A. Munchau, K.P. Bhatia, *Uses of Botulinum Toxin Injection in Medicine Today*, Clinical Review, British Medical Journal, vol. 320, p. 161–165, Jan. 15, 2000.

E. Schantz and E. Johnson, *Properties and Use of Botulinum Toxin and Other Microbial Neurotoxins in Medicine*, Microbiological Reviews, Mar. 1992, vol. 56, No. 1, p. 80–99.

K. Roger Aoki, *Pharmacology and Immunology of Botulinum Toxin Serotypes*, Journal of Neurology, Apr. 2001, 248 (Suppl 1); p. 1/3–1/10.

Aoki K. R., "Pharmacology and Immunology of Botulinum Toxin Serotypes", Journal of Neurology, vol. 248, Apr. 2001.

Munchau A., & Bhatia K.P., "Uses of Botulinum Toxin Injection in Medicine Today", British Medical Journal, vol. 319, No. 7228, Jan. 15, 2000.

Aoki, K.R.; *Preclinical Update on BOTOX® (Botulinum Toxin Type A)–Purified Neurotoxin Complex Relative to Other Botulinum Neurotoxin Preparations; European Journal of Neurology*; vol. 6 (suppl 4); S3–S10 (1999).

Boyd, R.S., et al.; *The Insulin Secreting B–Cell Line HIT–15 Contains SNAP–25 Which is a Target for Botulinum Neurotoxin–A; Movement Disorders*; vol. 10:3; Item 20; 376 (1995).

Cheshire, W.P., et al.; *Botulinum Toxin in the Treatment of Myofascial Pain Syndrome; Pain*; 59(1):65–69 (1994).

Dietz, F.R.; *Effect of Denervation on Limb Growth; Journal of Orthopaedic Research*; 7:292–303 (1989).

Erbguth, F.J., et al.; *Historical Aspects of Botulinum Toxin: Justinus Kerner (1786–1862) and the 'Sausage Poison; Neurology'*; 53:1850–1853 (1999).

Fauci, A.S., et al. (Editors); *Harrison's Principles of Internal Medicine*, 14$^{th}$ Edition; McGraw–Hill (1998).

Gonelle–Gispert, C., et al.; *SNAP–25a and —25b Isoforms are Both Expressed in Insulin Secreting Cells and Can Function in Insulin–Secretion; Biochem. J.*; 339:159–165 (1999).

Greco, F., et al.; *Nerve Fibres in Osteoid Osteoma; Int J Orthop Trauma*; 16:89–94 (1988).

Habermann, E.; *I–Labeled Neurotoxin from Clostridium Botulinum A: Preparation, Binding to Synaptosomes and Ascent to the Spinal Cord; Naunyn Schmiedeberg's Arch. Pharmacol.*; 281, 47–56 (1974).

Halperin, N., et al.; *Osteoid Osteoma of the Proximal Femur Simulating Spinal Root Compression; Clinical Orthopaedics and Related Research*; 162; p. 192–194 (1982).

Hasegawa, T., et al.; *Mechanism of Pain in Osteoid Osteomas: An Immunohistochemical Study; Histopathology*; 22:487–491 (1993).

Hukkanen, M., et al.; *Rapid Proliferation of Calcitonin Gene–Related Peptide–Immunoreactive Nerves During Healing of Rat Tibial Fracture Suggests Neural Involvement in Bone Growth and Remodelling; Neuroscience*; 54(4); 969–979 (1993).

Jaffe, H.L.; *"Osteoid–Osteoma"; Archives of Surgery*; 31; 709–728 (1935).

Lichtenstein, L.; *Classification of Primary Tumors of Bone; Cancer*; 335–341 (1951).

Mirra, J.; *Neurogenous Tumors; Bone Tumors: Clinical, Radiologic, and Pathologic Correlations*; Lea & Febiger publishers; vol. 1; Chapter 10; 801–867 (1989).

(List continued on next page.)

Primary Examiner—Anthony C. Caputa
Assistant Examiner—Misook Yu
(74) Attorney, Agent, or Firm—Martin A. Voet; Robert J. Baran; Carlos A. Fisher

(57) ABSTRACT

Methods for treating benign bone tumors by local administration to a patient of a therapeutically effective amount of a neurotoxin, such as a botulinum toxin, to alleviate pain associated with the bone tumor and/or to cause necrosis of the tumor.

17 Claims, No Drawings

OTHER PUBLICATIONS

Naumann, M., et al.; *Botulinum Toxin Type A in the Treatment of Focal, Axillary and Palmar Hyperhidrosis and Other Hyperhidrotic Conditions; European Journal of Neurology*; vol. 6, suppl. 4; S111–S115 (1999).

O'Connell, J.X., et al.; *Osteoid Osteoma: The Uniquely Innervated Bone Tumor; Modern Pathology*; 11(2); 175–180 (1998).

Poulain, B., et al.; *Inhibition of Transmitter Release by Botulinum Neurotoxin A; European Journal of Biochemistry*; 185:197–203 (1989).

Ragona, R.M., et al.; *Management of Parotid Sialocele with Botulinum Toxin; Laryngoscope*; 109; 1344–1346 (1999).

Schantz, E.J. et al.; *Properties and Use of Botulinum Toxin and Other Microbial Neurotoxins in Medicine; Microbiological Reviews*; vol. 56, No. 1; 80–99 (1992).

Schulman, L., et al.; *Nerve Fibers in Osteoid Osteoma; Journal of Bone and Joint Surgery*; 52–A(7); 1351–1356 (1970).

Sherman, M.S.; *The Nerves of Bone; Journal of Bone and Joint Surgery*; 45–A(3); 522–528 (1963).

Sherman, M.S., et al.; *Mechanism of Pain in Osteoid Osteomas; Southern Medical Journal*; 58; 163–166 (1965).

Singh, B.R.; *Critical Aspects of Bacterial Protein Toxins; Natural Toxins II*; Plenum Press, New York; pp. 63–84 (1996).

Susman, E.; *Botulinum—From Deadly Toxin to Therapeutic Weapon; Scrip Magazine*; p. 6–7 (Mar. 2000).

Wiegand, H., et al.; *I–Labelled Botulinum A Neurotoxin: Pharmacokineics in Cats After Intramuscular Injection; Naunyn–Schmiedeberg's Arch. Pharmacol.*; 292:161–165 (1976).

Williams, P.L., et al.; *Gray's Anatomy*; $38^{th}$ Edition; Churchill Livingstone, New York; p. 1469 (1995).

Zhou, L., et al.; *Expression and Purification of the Light Chain of Botulinum Neurotoxin A: A Single Mutation Abolishes Its Cleavage of SNAP–25 AND Neurotoxicity after Reconstitution with the Heavy Chain; Biochemistry*; 34:15175–15181 (1995).

Bagshawe, K.D., et al.; *Antibody Directed Enzyme Prodrug Therapy(Adept): Clinical Report; Disease Markers*; vol. 9:233–238 (1991).

Bagshawe, K.D., et al.; *A Cytotoxic Agent can be Generated Selectively at Cancer Sites; Br. J. Cancer*; 58:700–703 (1988).

Bigalke, H., et al.; *Botulinum A Neurotoxin Inhibits Non–Cholinergic Synaptic Transmission in Mouse Spinal Cord Neurons in Culture; Brain Research*; 360 (1985); 318–324.

Bigalke, H., et al.; *Tetanus Toxin and Botulinum A. Toxin Inhibit Release and Uptake of Various Transmitters, as Studied with Particulate Preparations from Rat Brain and Spinal Cord; Naunyn–Schmiedeberg's Arch. Pharmacol*; (1981); 316:244–251.

Bryan, M.; *Glomus Tumors; Dept. of Otolaryngology, UTMB*; 10 pages (Jan. 11, 1995); www.utmb.edu/oto/Grnds.dir/glomus.htm.

Col, V., et al.; *Heart Failure Induced by Pheochromocytoma: Laparoscopic Treatment and Intraoperative Changes of Several New Cardiovascular Hormones; Hormone Research*; (1999); 51:50–52.

Eccles, S.A., et al.; *Regression of Established Breast Carcinoma Xenografts with Antibody–Directed Enzyme Prodrug Therapy Against c–erbB2; Cancer Research*; 54:5171–5177 (Oct. 1, 1994); p. 185.

Habermann, E., et al.; *Tetanus Toxin and Botulinum A and C Neurotoxins Inhibit Noradrenaline Release from Cultured mouse Brain; Journal of Neurochemistry*; vol. 51; No. 2 (1988); 522–527.

Heppner, F.; *New Technologies to Combat malignant Tumours of the Brain; Anticancer Research*; 2:101–110 (1982).

Heppner and Mose; *The Liquefaction (Oncolysis) of Malignant Gliomas by a Non Pathogenic Clostridium; Acta Neurochir*; 42(1–2); 123–5.

Jankovic, J., et al., editors; *Therapy with Botulinum Toxin*; Marcel Dekker, Inc. publisher; p. 45 (1994).

John, H., et al.; *Pheochromocytomas: Can Malignant Potential be Predicted:?; Urology*; (1990); 53(4): 679–683.

Johnson, R. et al.; *The Clinical Impact of Screening and Other Experimental Tumor Studies; Cancer Treatment Reviews*; (1975); 2: 1–31.

Laskawi, R., et al.; *Up–of–date Report to Botulinum Toxin Type A Treatment in Patients with Gustatory Sweating (Frey's Syndrome); The Laryngoscope*; (Mar. 1998); 108:381–384.

Lemmon, M.J., et al.; *Anaerobic Bacteria as a Gene Delivery System to Tumors; Proceedings of the American Association for Cancer Research*; vol. 35:374 (Mar. 1994); Abstract No. 2231.

Lin, J.C., et al.; *Cardiac Pheochromocytoma: Resection After Diagnosis by 111–Indium Octreotide Scan; Ann Thorac Surg*; (1999); 67:555–558.

Minton, et al.; *Chemotherapeutic Tumour Targeting Using Clostridial Spores; FEMS Microbiology Reviews*; 17 (1995):357–364.

Naumann, M., et al.; *Botulinum Toxin in the Treatment of Neurological Disorders of the Autonomic Nervous System; Arch Neurol*; (Aug. 1999); 56:914–916.

Sanchez–Prieto, J., et al.; *Botulinum Toxin A Blocks Glutamate Exocytosis from Guinea–Pig Cerebral Cortical Synaptosomes; Eur. J. Biochem.*; (1987); 165:675–681.

Schweitzer, E.S., et al.; *Inhibition of Regulated Catecholamine Secretion from PC12 Cells by the $Ca^{2}$ ⁺/*Calmodulin Kinase II Inibitor KN–62; *Journal of Cell Science*; (1995); 108:2619–2628.

Sigma; *Biochemicals and Reagents for Life Science Research*; p. 187–188.

Springer, C.J., et al.; *Ablation of Human Choriocarcinoma Xenografts in Nude Mice by Antibody–Directed Enzyme Prodrug Therapy (ADEPT) with Three Novel Compounds; Eur. J. Cancer*; 27 (11): 1361–1366 (1991).

Walther, M.M., et al.; *Pheochromocytoma: Evaluation, Diagnosis, and Treatment; World J Urol*: (1999); 17:35–39.

Warwar, R.E., et al.; *Coexistence of 3 Tumors of Neural Crest Origin Neurofibroma, Meningioma, and Uveal Malignant Melanoma; Arch Ophthalmol*; (Sep. 1998); 116:1241–1243.

Williamson, L.C., et al.; *Clostridial Neurotoxins and Substrate Proteolysis in Intact Neurons; The Journal of Biological Chemistry*; (Mar. 29, 1996); vol. 271, No. 13:7694–7699.

Xu, T., et al.; *Kinetic Studies of Ca2+ Binding and Ca2+ Clearance in the Cytosol of Adrenal Chromaffin Cells; Biophysical Journal*; vol. 73:532–545 (Jul. 1997).

Xu, T., et al.; *Multiple Kinetic Components of Exocytosis Distinguished by Neurotoxin Sensitivity; Nature Neuroscience*; 1(3): 192–200; (Jul. 1998).

* cited by examiner

METHODS FOR TREATING BONE TUMORS

BACKGROUND

The present invention relates to methods for treating bone tumors. In particular, the present invention relates to methods for treating pain associated with a bone tumor by local administration of a neurotoxin.

The bones of the mammalian skeleton are covered by a thick, fibrous membrane, the periosteum. Except for the richly innervated periosteum, bone is relatively insensitive to painful stimuli and surgical trauma can usually be inflicted upon bone with little or no patient discomfort. Even though bone is generally insensitive to pain, nerve fibers exist in bone, usually closely associated with blood vessels. Sherman, M. S. et al *The Nerves of Bone,* J. Bone & Joint Surgery, 45-A(3);522–528:1963. The nerves in bone are apparently derived from the autonomic system and influence intraosseal blood flow as well as sensation of pressure and position. Halperin N., et al. *Osteoid Osteoma of the Proximal Femur Simulating Spinal Root Compression,* Clinical Orthopaedics & Related Research, 162;191–194;1982.

Thus, it is known that both bone and periosteum have both afferent sensory and efferent autonomic innervation. Hukkanen M., et al, *Rapid Proliferation of Calcitonin Gene-Related Peptide-Immunoreactive Nerves During Healing of Rat Tibial Fracture Suggests Neural Involvement in Bone Growth and Remodelling,* Neuroscience 54(4);969–979:1993. See also O'Connell J. X. et al, *Osteoid Osteoma: The Uniquely Innervated Bone Tumor,* Mod Pathol 11(2);175–180:1998.

The non-myelinated axons found in bone are apparently postganglionic fibers derived from sympathetic ganglia and act upon vasoconstrictor or vasodilatory fibres in bone blood vessel walls. Bone nerves can also comprise post-ganglionic parasympathetic fibers, which are also usually non-myelinated, as well as being cholinergic. Significantly, sympathetic, cholinergic vasodilatory nerve fibers in association with blood vessels have been reported. Schulman L., et al., *Nerve Fibers in Osteoid Osteoma,* J. Bone & Joint Surgery, 52-A(7);1351–1356:1970. See also page 1469 of Williams P. L., et al, *Gray's Anatomy,* 38$^{th}$ Edition (1995), Churchill Livingstone, N.Y.

Bone tumors can arise from bone tissues as well as from nerves located within bone. Lichtenstein, L., *Classification of Primary Tumors of Bone,* Cancer 335–341;1951. Benign bone tumors of cartilaginous origin include enchondroma, osteochondroma, chondroblastoma and chondromyxoid. Benign bone tumors of bone tissue proper origin include osteoid osteoma and osteoblastoma.

Nerve fibers have been demonstrated within various bone tumors, including in the nidus of osteoid osteomas and in osteoblastomas. Schulman L. et al, *Nerve Fibers in Osteoid Osteoma,* J. Bone & Joint Surgery, 52-A(7); 1351–1356:1970. The nerve fibers within bone tumors are predominately non-myelinated, hence presumably arising from the sympathetic and/or parasympathetic nervous systems and are believed to have at least a vasomotor action upon tumor blood vessels. Additionally, myelinated nerve fibers located within bone tumors are postulated to function as afferent nociceptors. Greco F., et al., *Nerve Fibres in Osteoid Osteoma,* Int. J. Orthop Trauma, 16; 89–94:1988.

Typically, an intramedullary neoplasm will remain asymptomatic, even if rather large, until it breaks through the bone and contacts the periosteum. Osteoid osteomas are small and benign and richly vascularized bone neoplasms. Osteoid osteomas are rarely greater than one or two centimeters in diameter. Though surrounded by bone tissue and not in contact with the periosteum, even a small osteoid osteoma can cause intense throbbing pain. The pain generated by the presence of an osteoid osteoma can generally be relieved, at least to some extent, by oral salicyliates, such as aspirin. The pain can be described as local and more severe at night. Jaffe, H. L. *Osteoid-Osteoma, Arch Surg* 31;709–728:1935. Pain generated by a bone tumor if ineffectively treated can limit function, reduce mobility, complicate sleep, and dramatically interfere with the quality of life.

It has been hypothesized that the pain which accompanies osteoid osteoma is due to vascular pressure changes within the neoplasm, presumably by direct stimulation of local nerves around intraosseous vessels. Sherman, M. S. et al, *Mechanism of Pain in Osteoid Osteomas,* Southern Medical Journal 58;163–166:1965.

Present methods for treating bone tumors, whether by drugs or surgery, have many drawbacks and deficiencies. Thus, the typical oral, parenteral or topical administration of an analgesic drug (such as a NSAID) to treat the symptoms of pain or of, for example, a salicylate, can result in widespread systemic distribution of the drug and undesirable side effects. Additionally, current drug therapy for bone tumor pain suffers from short drug efficacy durations which necessitate frequent drug re-administration with possible resulting drug resistance, antibody development and/or drug dependence and addiction, all of which are unsatisfactory. Furthermore, frequent drug administration increases the expense of the regimen to the patient and can require the patient to remember to adhere to a dosing schedule.

Surgical excision is unnecessary in the case of a benign bone tumor and should be avoided to prevent the bone destruction inevitable upon surgical removal and to avoid the risks attendant to surgical intervention. Additionally, surgery for a benign neoplasm can be refused by the patient or be contraindicated in a frail, elderly or osteoporeitic patient. Furthermore, the intramedullary nature of certain bone tumors can render them inoperable.

Botulinum Toxin

The anaerobic, gram positive bacterium Clostridium botulinum produces a potent polypeptide neurotoxin, botulinum toxin, which causes a neuroparalytic illness in humans and animals referred to as botulism. The spores of Clostridium botulinum are found in soil and can grow in improperly sterilized and sealed food containers of home based canneries, which are the cause of many of the cases of botulism. The effects of botulism typically appear 18 to 36 hours after eating the foodstuffs infected with a Clostridium botulinum culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (available from Allergan, Inc., of Irvine, Calif. as a purified neurotoxin complex under the tradename BOTOX®) is a $LD_{50}$ in mice (i.e. 1 unit). Thus, one unit of BOTOX® contains about 50 picograms of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins,* pages 63–84 (chapter 4) of Natural Toxins II, edited by B. R. Singh et al., Plenum Press, New York (1996) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

Seven immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Botulinum toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin/B/D,/F, and/G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Serotype A and E cleave SNAP-25. Serotype $C_1$ was originally thought to cleave syntaxin, but was found to cleave syntaxin and SNAP-25. Each toxin specifically cleaves a different bond (except tetanus and type B which cleave the same bond).

Botulinum toxins have been used in clinical settings for the treatment of neuromuscular disorders characterized by hyperactive skeletal muscles. Botulinum toxin type A has been approved by the U.S. Food and Drug Administration for the treatment of blepharospasm, strabismus and hemifacial spasm. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Significantly, it is known that the cytosol of pancreatic islet B cells contains at least SNAP-25 (Biochem J 1;339 (pt 1): 159–65 (April 1999)), and synaptobrevin (Mov Disord May 10, 1995(3): 376).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ are apparently produced as only a 500 kD complexes. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from the site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

Botulinum toxin type A can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of Clostridium botulinum with characteristics of $\geq 3 \times 10^7$ U/mg, an $A_{260}/A_{278}$ of less than 0.60 and a distinct pattern of banding on gel electrophoresis. The known Shantz process can be used to obtain crystalline botulinum toxin type A, as set forth in Shantz, E. J., et al, *Properties and use of Botulinum toxin and Other Microbial Neurotoxins in Medicine,* Microbiol Rev. 56: 80–99 (1992). Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1-2 \times 10^8$ $LD_{50}$ U/mg or greater; purified botulinum toxin type B with an approximately 156 kD molecular weight with a specific potency of $1-2 \times 10^8$ $LD_{50}$ U/mg or greater, and; purified botulinum toxin type F with an approximately 155 kD molecular weight with a specific potency of $1-2 \times 10^7$ $LD_{50}$ U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo.

Pure botulinum toxin is so labile that it is generally not used to prepare a pharmaceutical composition. Furthermore, the botulinum toxin complexes, such a the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin must be stabilized with a stabilizing agent. The only successful stabilizing agent for this purpose has been the animal derived proteins albumin and gelatin. And as indicated, the presence of animal derived proteins in the final formulation presents potential problems in that certain stable viruses, prions or other infectious or pathogenic compounds carried through from donors can contaminate the toxin.

Furthermore, any one of the harsh pH, temperature and concentration range conditions required to lyophilize (freeze-dry) or vacuum dry a botulinum toxin containing pharmaceutical composition into a toxin shipping and storage format (ready for use or reconstitution by a physician) can detoxify some of the toxin. Thus, animal derived or donor pool proteins such as gelatin and serum albumin have been used with some success to stabilize botulinum toxin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of Clostridium botulinum grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. BOTOX® can be reconstituted with sterile, non-preserved saline prior to intramuscular injection. Each vial of BOTOX® contains about 100 units (U) of Clostridium botulinum toxin type A purified neurotoxin complex, 0.5 milligrams of human serum albumin and 0.9 milligrams of sodium chloride in a sterile, vacuum-dried form without a preservative.

To reconstitute vacuum-dried BOTOX® sterile normal saline without a preservative; 0.9% Sodium Chloride Injection is used by drawing up the proper amount of diluent in the appropriate size syringe. Since BOTOX® is believed to be denatured by bubbling or similar violent agitation, the diluent is gently injected into the vial. BOTOX® should be administered within four hours after reconstitution. During this time period, reconstituted BOTOX® is stored in a refrigerator (2° to 8° C.). Reconstituted BOTOX® is clear, colorless and free of particulate matter. The vacuum-dried product is stored in a freezer at or below −5° C. BOTOX® is administered within four hours after the vial is removed from the freezer and reconstituted. During these four hours, reconstituted BOTOX® can be stored in a refrigerator (2° to 8° C.). Reconstituted BOTOX® is clear, colorless and free of particulate matter.

It has been reported that botulinum toxin type A has been used in clinical settings as follows:

(1) about 75–125 units of BOTOX® per intramuscular injection (multiple muscles) to treat cervical dystonia;

(2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
   (a) flexor digitorum profundus: 7.5 U to 30 U
   (b) flexor digitorum sublimus: 7.5 U to 30 U
   (c) flexor carpi ulnaris: 10 U to 40 U
   (d) flexor carpi radialis: 15 U to 60 U
   (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (*European J. Neurology* 6 (Supp 4): S111–S115:1999), and in some circumstances for as long as 27 months. The *Laryngoscope* 109: 1344–1346:1999. However, the usual duration of a therapeutic effect of an intramuscular injection of Botox® is typically about 3 to 4 months.

Certain botulinum toxins have been used to treat various movement disorders, such as spasmodic muscle conditions with a resulting alleviation of pain. For example, it is known to use a botulinum toxin to treat muscle spasms with resulting relief from both the spasmodic muscle hyperactivity and from the pain which secondarily arises as a result of or due to the spasmodic muscle activity. For example, Cheshire et al., *Pain*, 59(1);65–69:1994 reported that patients with myofascial pain syndrome experienced a reduction of pain after injections of botulinum toxin type A to trigger points. See also WO 94/15629. It is believed that botulinum toxin A can reduce pain by reducing the sustained muscle contraction that caused or that substantially caused the pain in the first place. Thus, the pain which can result from or which can accompany a muscle spasm can be due to the lower, local pH caused by the spasm. An indirect effect of the flaccid muscle paralysis induced by a botulinum toxin is to permit the pH to return to a physiological level, thereby causing pain reduction as a secondary effect of the motor endplate cholinergic denervation which can result due to peripheral botulinum toxin administration.

Botulinum toxin can be used to treat migraine headache pain that is associated with muscle spasm, vascular disturbances, neuralgia and neuropathy. See e.g. U.S. Pat. No. 5,714,468. Notably, muscle spasm pain, hypertonic muscle pain, myofascial pain and migraine headache pain can all be due, at least in part, to the production and release of one or more nociceptive substances from the muscles themselves during periods of increased muscle tension or contraction.

The success of botulinum toxin type A to treat a variety of clinical conditions has led to interest in other botulinum toxin serotypes. A study of two commercially available botulinum type A preparations (BOTOX® and Dysport®) and preparations of botulinum toxins type B and F (both obtained from Wako Chemicals, Japan) has been carried out to determine local muscle weakening efficacy, safety and antigenic potential. Botulinum toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or botulinum toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for botulinum toxin type B or 0.15 ng/kg for BOTOX®). Peak muscle weakness and duration were dose related for all serotypes. DAS $ED_{50}$ values (units/kg) were as follows: BOTOX®: 6.7, Dysport®: 24.7, botulinum toxin type B: 27.0 to 244.0, botulinum toxin type F: 4.3. BOTOX® had a longer duration of action than botulinum toxin type B or botulinum toxin type F. Therapeutic index values were as follows: BOTOX®: 10.5, Dysport®: 6.3, botulinum toxin type B: 3.2. Water consumption was greater in mice injected with botulinum toxin type B than with BOTOX®, although botulinum toxin type B was less effective at weakening muscles. After four months of injections 2 of 4 (where treated with 1.5 ng/kg) and 4 of 4 (where treated with 6.5 ng/kg) rabbits developed antibodies against botulinum toxin type B. In a separate study, 0 of 9 BOTOX® treated rabbits demonstrated antibodies against botulinum toxin type A. DAS results indicate relative peak potencies of botulinum toxin type A being equal to botulinum toxin type F, and botulinum toxin type F being greater than botulinum toxin type B. With regard to duration of effect, botulinum toxin type A was greater than botulinum toxin type B, and botulinum toxin type B duration of effect was greater than botulinum toxin type F. As shown by the therapeutic index values, the two commercial preparations of botulinum toxin type A (BOTOX® and Dysport®) are different. The increased water consumption behavior observed following hind limb injection of botulinum toxin type B indicates that clinically significant amounts of this serotype entered the murine systemic circulation. The results also indicate that in order to achieve efficacy comparable to botulinum toxin type A, it is necessary to increase doses of the other serotypes examined. Increased dosage can comprise safety.

Furthermore, in rabbits, type B was more antigenic than was BOTOX®, possibly because of the higher protein load injected to achieve an effective dose of botulinum toxin type B. *Eur J Neurol* 1999 Nov;6(Suppl 4):S3-S10.

In addition to having pharmacologic actions at the peripheral location, botulinum toxins may also have inhibitory effects in the central nervous system. Work by Weigand et al, *Nauny-Schmiedeberg's Arch. Pharmacol.* 1976; 292, 161–165, and Habermann, *Nauny-Schmiedeberg's Arch. Pharmacol.* 1974; 281, 47–56 showed that botulinum toxin is able to ascend to the spinal area by retrograde transport. As such, a botulinum toxin injected at a peripheral location, for example, intramuscularly, may be retrogradely transported to the spinal cord. However, the authors of the cited articles were unable to demonstrate that the radiolabelled material was intact botulinum toxin.

As discussed above, pain associated with muscle disorder, for example muscle spasm pain, and headache pain associated with vascular disturbances, neuralgia and neuropathy may be effectively treated by the use of botulinum toxin. However, there is a clear deficiency in available means for the treatment of an array of other types of pain. Such pain include, for example, pain associated with a bone tumor.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine What is needed therefore is an effective, long lasting, non-surgical method to treat pain associated with a bone tumor and to treat the bone tumor itself.

SUMMARY

The present invention meets this need and provides an effective, long lasting, non-surgical method to treat a bone tumor.

Definitions

The following definitions apply herein:

"About" means approximately or nearly and in the context of a numerical value set forth herein means ±10% of the numerical value or range recited or claimed.

"Biological activity" means, with regard to a neurotoxin, the ability to reduce neurotransmission at synapses having acetylcholine receptors by reducing acetylcholine release from nerve endings.

"Bone tumor" means a neoplasm located on or within a bone.

"Local administration" means direct administration by a non-systemic route at or in the vicinity of the site of an affliction, disorder or perceived pain.

"Neurotoxin" means a biologically active molecule with a specific affinity for a neuronal cell receptor. Neurotoxin includes Clostridial toxins both in pure toxin and as complexed with one or more non-toxin, toxin associated proteins.

A method for treating a bone tumor within the scope of the present invention has the step of local administration of a neurotoxin to a bone tumor or to the vicinity of a bone tumor, thereby reducing pain associated with, arising from or due to the bone tumor. The neurotoxin can be a botulinum toxin, such as a botulinum toxin selected from the group consisting of botulinum toxin types A, B, $C_1$, D, E, F and G. Preferably, the botulinum toxin is a botulinum toxin type A.

The neurotoxin can be a modified neurotoxin having at least one amino acid deleted, modified or replaced and the neurotoxin can be made, at least in part, by a recombinant process.

Preferably, the neurotoxin is administered in an amount between about 0.01 U/kg and about 200 U/kg and the pain is substantially alleviated, upon local administration of a neurotoxin to a painful bone tumor, for between about 1 month and about 30 months, or longer. In a more preferred embodiment the neurotoxin can be administered in an amount between about 0.01 U/kg and about 35 U/kg. The local administration can be carried out, for example, by injection of the neurotoxin or the local administration can be carried out by insertion of a neurotoxin containing implant.

A detailed embodiment within the scope of the present invention can be of a method for treating a bone tumor by local administration of a botulinum toxin to a bone tumor or to the vicinity of the bone tumor of a human patient, thereby substantially alleviating pain associated with or arising from the bone tumor.

Significantly, a method within the scope of the present invention for treating a benign bone tumor by local administration of a neurotoxin to a benign bone tumor or to the vicinity of the bone tumor can cause or result in a reduction in the size (diameter) of the benign bone tumor. The benign bone tumor can be an osteoid osteoma and the diameter of such a benign bone tumor can be reduced by between about 20% and about 100% subsequent to the local administration of the neurotoxin.

Thus, a detailed embodiment within the scope of the present invention can be a method for treating a benign bone tumor, the method comprising the step of local administration of a therapeutic amount of a botulinum toxin to a benign bone tumor or to the vicinity of a bone tumor, thereby causing a reduction in the diameter of the benign bone tumor of between about 20% and about 100%.

The present invention also encompasses a method for improving patient function, the method comprising the step of local administration of a botulinum toxin to a bone tumor or to the vicinity of the bone tumor, thereby improving patient function as determined by improvement in one or more of the factors of reduced pain, reduced time spent in bed, improved healing, increased ambulation, healthier attitude and a more varied lifestyle.

DESCRIPTION

The present invention is based upon the discovery that local administration of a neurotoxin can alleviate pain associated with a bone tumor. Additionally, it has also been discovered that local administration of a neurotoxin to a bone tumor can cause a reduction in the size of the bone tumor.

According to the present invention, a neurotoxin, such, as a botulinum toxin locally administered to a bone tumor can substantially alleviate pain due to the presence of the tumor. Without wishing to be bound by theory, a mechanism can be postulated for this antinociceptive effect. Thus, it is known that axons from the principal sympathetic ganglionic cells have non-myelinated, postganglionic fibres and can supply vasoconstrictor or vasodilatory fibres to blood vessels. Additionally, it is known that post-ganglionic parasympathetic fibers are also usually non-myelinated and cholinergic. Significantly, sympathetic, cholinergic vasodilatory nerve fibers in association with blood vessels have also been identified.

Hence, pain associated with certain innervated bone tumors (such as the highly vascularized osteoid osteoma) can be due to cholinergicly mediated dilation of blood vessels which supply the tumor. The expanded vessels compress neighboring tissues, or by direct impingement, stimulate afferent nociceptors associated with the tumor, thereby resulting in the transmission of pain signals and hence a perception of pain at the location of the tumor or in its vicinity.

Upon local administration of a neurotoxin, such as a botulinum toxin, pain reduction can occur due to the induced chemical denervation of cholinergic vasomotor neurons at or in the vicinity of the bone tumor. Tumor necrosis can also occur because by preventing vasodilation the chemical denervation reduces blood supply to the tumor. Thus, the abundant innervation associated with nutrient arteries observed in bone tumors, such as osteoid osteomas, can be chemically denervated thereby preventing optimal vessel flow to the tumor, and resulting in pain reduction and/or tumor size reduction.

According to one aspect of the invention, there are provided methods for treatment of pain which comprise locally administering directly to a painful, benign bone tumor of a human patient therapeutically effective doses of a neurotoxin, for example a Clostridial neurotoxin. The neurotoxin can be selected from a group consisting of Clostridial beratti, butyricum, botulinum and/or tetani toxin. In accordance with the present invention, any of the known botulinum toxin serotypes A to G or other serotype having a substantially equivalent biological activity can be used to treat a bone tumor. Thus, a neurotoxin administered to a bone tumor of a patient can be selected from a group consisting of botulinum toxin types A, B, $C_1$, D, E, F, or G.

Preferably, because of its ready availability and clinical history to successfully treat a number of indications, a method within the scope of the present invention includes local administration of a botulinum type A. A botulinum toxin type A used in a method within the scope of the present invention can be a complex of toxin and non-toxin proteins, which together comprise a total molecular weight of about 900 kiloDaltons and which is used at a concentration of between about 10 and about 500 units per bone tumor injected. A botulinum toxin type B used in a method within the scope of the present invention can be a complex of toxin and non-toxin proteins, which together comprise a total molecular weight of about 700 kiloDaltons and which is used at a concentration of between about 100 and about 20,000 units per bone tumor injected.

Other botulinum toxin serotypes can be used in proportion to the dosages and concentrations exemplified herein, according to their respective levels of biological activity. The present invention also encompasses methods for concurrent or serial administration of a mixture of two or more of the above neurotoxins to effectively treat a patient with a bone tumor.

Examples of neoplasms which can be treated according to the present invention are benign bone tumors of cartilaginous origin such as enchondroma, osteochondroma, chondroblastoma and chondromyxoid, all of cartilaginous origin, as well as benign bone tumors of bone origin including osteoid osteoma and osteoblastoma. A neurotoxin, such as a botulinum toxin can require, according to the methods of the present invention, from about 1 to 7 days to achieve an antinociceptive effect or to begin to achieve a necrotic effect upon a bone tumor. Thus, malignant bone tumors are excluded from the scope of the present invention because such tumors are preferably treated by a protocol with immediate effect such as surgical excision or radiotherapy, so as to prevent the tumor metastasizing.

Additionally a neurotoxin according to the present invention is always locally administered in vivo directly to the site of the tumor, whether on or within a bone. Known local drug administration methods suitable for this purpose include by long needle for bolus injection and by insertion of a controlled release implant. Systemic routes of drug administration such as oral or intravenous administration are excluded from the scope of the present invention because systemic distribution of a neurotoxin is not desirable.

In another embodiment, the methods comprise the administration of a neurotoxin, for example a Clostridial neurotoxin, to a patient wherein the neurotoxin differs from a naturally occurring neurotoxin by at least one amino acid. For example, variants of botulinum toxin type A as disclosed in *Biochemistry* 34;5175–15181:1995 and *Eur. J. Biochem,* 185;197–203:1989 can be administered. Practice of the present invention can provide an analgesic effect, per injection, for 2 to 30 months or longer in humans.

The amount of the neurotoxin administered can vary widely according to the particular disorder being treated, its severity and other various patient variables including size, weight, age, and responsiveness to therapy. Generally, the dose of neurotoxin to be administered will vary with the age, presenting condition and weight of the mammal to be treated. The potency of the neurotoxin to be administered is also a consideration.

In one embodiment according to this invention, the therapeutically effective doses of a neurotoxin, for example a botulinum toxin type A complex, can be between about 0.01 U/kg and about 35 U/kg. Less than about 0.01 U/kg can result in a suboptimal antinociceptive effect while more than about than about 35 U/kg can approach a toxic dose.

Although examples of routes of administration and dosages are provided, the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill). For example, the route and dosage for administration of a neurotoxin according to the present disclosed invention can be selected based upon criteria such as the solubility characteristics of the neurotoxin chosen as well as the intensity of pain perceived.

The neurotoxin may be obtained by culturing an appropriate bacterial species. For example, botulinum toxin type A can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

If a modified neurotoxin is to be used according to this invention to treat non-spasm related pain, recombinant techniques can be used to produce the desired neurotoxins. The technique includes steps of obtaining genetic materials from natural sources, or synthetic sources, which have codes for a neuronal binding moiety, an amino acid sequence effective to translocate the neurotoxin or a part thereof, and an amino acid sequence having therapeutic activity when released into a cytoplasm of a target cell, preferably a neuron.

A method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assesses using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

EXAMPLES

The following examples provide those of ordinary skill in the art with specific preferred methods within the scope of the present invention to treat a bone tumor and are not intended to limit the scope of the invention.

Example 1

Treatment of Osteoid Osteoma with Botulinum Toxin Type A

A 24 year old female presents with a four month history of pain in the right buttock radiating to the lateral aspect of her thigh and leg. The pain is throbbing in nature and awakens her at night. It is aggravated by exercise and partially alleviated by aspirin. Examination reveals a full range of hip motion. Routine lab values (hematocrit, WBC, etc) and CSF content are normal. Pelvic X-rays reveal a small, oval lesion at the base of the right femoral neck. A diagnosis of osteoid osteoma is made. Under radiographic guidance 50 units of BOTOX® is injected directly into the tumor. Within 1 to 7 days the pain has been substantially alleviated and the patient remains asymptomatic thereafter. Radiography and bone aspiration biopsy at 3 months post injection fails to reveal any evidence of the neoplasm.

Example 2

Treatment of Osteoid Osteoma with Botulinum Toxin Type B

A 13 year old boy is admitted with a three month history of gnawing, persistent pain in his left thigh. The pain is more pronounced at night. Both the boy and his parents deny trauma. Physical examination reveals a healthy boy in no acute distress. Both hip joints have a full range of motion. The left thigh is tender. The left patellar reflex is absent and the ankle jerk somewhat diminished. Plantar responses are both flexor. Routine lab values, electromyography, spinal fluid content and pantopaque myelography are all normal. X-rays reveal a small, oval, lytic lesion situated below the lesser trochanter. A diagnosis of osteoid osteoma is made. 2500 units of a botulinum type B preparation is injected directly into the tumor. Within 1 to 7 days the pain has been substantially alleviated and the patient remains asymptomatic. Radiography and bone aspiration biopsy at 3 months post injection fails to reveal any evidence of the neoplasm.

Example 3

Treatment of Osteoid Osteoma with Botulinum Toxin Type C

A 58 year old female is diagnosed with osteoid osteoma. Between about $10^{-3}$ U/kg and about 35 U/kg of a botulinum toxin type C preparation (for example between about 10 units and about 10,000 units of a botulinum type C preparation) is injected directly into the tumor. Within 1 to 7 days the pain has been substantially alleviated and the patient remains asymptomatic. Radiography and bone aspiration biopsy at 3 months post injection fails to reveal any evidence of the neoplasm.

Example 4

Treatment of Osteoid Osteoma with Botulinum Toxin Type D

A 56 year old obese female is diagnosed with osteoid osteoma. Between about $10^{-3}$ U/kg and about 35 U/kg of a botulinum toxin type D preparation (for example between about 10 units and about 10,000 units of a botulinum type D preparation) is injected directly into the tumor. Within 1 to 7 days the pain has been substantially alleviated and the patient remains asymptomatic. Radiography and bone aspiration biopsy at 3 months post injection fails to reveal any evidence of the neoplasm.

Example 5

Treatment of Osteoid Osteoma with Botulinum Toxin Type E

A 61 year old female is diagnosed with osteoid osteoma. Between about $10^{-3}$ U/kg and about 35 U/kg of a botulinum toxin type E preparation (for example between about 10 units and about 10,000 units of a botulinum type E preparation) is injected directly into the tumor. Within 1 to 7 days the pain has been substantially alleviated and the patient remains asymptomatic. Radiography and bone aspiration biopsy at 3 months post injection fails to reveal any evidence of the neoplasm.

Example 6

Treatment of Osteoid Osteoma with Botulinum Toxin Type F

A 52 year old male is diagnosed with osteoid osteoma. Between about $10^{-3}$ U/kg and about 35 U/kg of a botulinum toxin type F preparation (for example between about 10 units and about 10,000 units of a botulinum type F preparation) is injected directly into the tumor. Within 1 to 7 days the pain has been substantially alleviated and the patient remains asymptomatic. Radiography and bone aspiration biopsy at 3 months post injection fails to reveal any evidence of the neoplasm.

Example 7

Treatment of Osteoid Osteoma with Botulinum Toxin Type G

A 14 year old male is diagnosed with osteoid osteoma. Between about $10^{-3}$ U/kg and about 35 U/kg of a botulinum toxin type G preparation (for example between about 10 units and about 10,000 units of a botulinum type G preparation) is injected directly into the tumor. Within 1 to 7 days the pain has been substantially alleviated and the patient remains asymptomatic. Radiography and bone aspiration biopsy at 3 months post injection fails to reveal any evidence of the neoplasm.

Example 8

Treatment of Osteoblastoma with Botulinum Toxin Type A–G

A 19 year old male presents with a two month history of persistent pain in the right shoulder Examination reveals a full range of shoulder motion. Routine lab values (hematocrit, WBC, etc) and CSF content are normal. X-rays reveal a small, oval lesion at the base of the scapula and exploratory biopsy confirms a diagnosis of osteoblastoma. Under radiographic guidance between about $10^{-3}$ U/kg and about 200 U/kg of a botulinum toxin preparation type A, B, $C_1$, D, E, F or G (for example about 50 units of BOTOX®) is injected directly into the tumor. Within 1 to 7 days the pain has been substantially alleviated and the patient remains asymptomatic. Radiography and bone aspiration biopsy at 3 months post injection fails to reveal any evidence of the neoplasm.

Methods according to the invention disclosed herein has many advantages, including the following:

(1) the invention renders unnecessary many surgical procedures for effective treatment of a benign bone tumor.

(2) systemic drug effects can be avoided by direct local application of a neurotoxin according to the present invention.

(3) the ameliorative effects of the present invention can persist from about 2 months to about 6 months, or longer, from a single local administration of a neurotoxin as set forth herein, and can be permanent upon necropsy of the tumor.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes peripheral administration methods to treat bone tumors wherein two or more neurotoxins, such as two or more botulinum toxins, are administered concurrently or consecutively. For example, botulinum toxin type A can be administered until a loss of clinical response or neutralizing antibodies develop, followed by administration of botulinum toxin type E. Alternately, a combination of any two or more of the botulinum serotypes A–G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a botulinum toxin, begins to exert its therapeutic effect. All patents, publications and articles cited above are incorporated herein in their entireties.

I claim:

1. A method for treating a bone tumor, the method comprising the step of local administration of a neurotoxin to a bone tumor, thereby reducing pain associated with the bone tumor, wherein the local administration is carried out by insertion of a neurotoxin containing implant.

2. The method of claim 1, wherein the neurotoxin is a botulinum toxin.

3. The method of claim 1, wherein the neurotoxin is a botulinum toxin selected from the group consisting of botulinum toxin types A, B, $C_1$, D, E, F and G.

4. The method of claim 1, wherein the neurotoxin is botulinum toxin type A.

5. The method of claim 1, wherein the neurotoxin is made at least in part by a recombinant process.

6. The method of claim 1, wherein the neurotoxin is administered in an amount between about 0.01 U/kg and about 200 U/kg.

7. The method of claim 1, wherein the pain is substantially alleviated for between about 1 month and about 30 months.

8. A method for treating a bone tumor, the method comprising the step of local administration of a botulinum toxin to a bone tumor to a human patient, thereby substantially alleviating pain associated with or arising from the bone tumor, wherein the local administration is carried out by insertion of a botulinum toxin containing implant.

9. The method of claim 8, wherein the botulinum toxin is selected from the group consisting of botulinum toxin types A, B, $C_1$, D, E, F, and G.

10. A method for treating a benign bone tumor, the method comprising the step of local administration of a neurotoxin to a benign bone tumor, thereby causing a reduction in the size of the benign bone tumor, wherein the local administration is carried out by insertion of a neurotoxin containing implant.

11. The method of claim 10, wherein the benign bone tumor is an osteoid osteoma.

12. The method of claim 10, wherein the neurotoxin is a botulinum toxin.

13. The method of claim 10, wherein the diameter of the benign bone tumor is reduced by between about 20% and about 100% subsequent to the local administration of the neurotoxin.

14. A method for treating a benign bone tumor, the method comprising the step of local administration of a therapeutic amount of a botulinum toxin to a benign bone tumor, thereby causing a reduction in the diameter of the benign bone tumor of between about 20% and about 100%, wherein the local administration is carried out by insertion of a botulinum toxin containing implant.

15. A method for improving patient function, the method comprising the step of local administration of a botulinum toxin to a bone tumor, thereby improving patient function as determined by improvement in one or more of the factors of reduced pain, reduced time spent in bed, improved healing, increased ambulation, improved mental health and decreased role limitations, wherein the local administration is carried out by insertion of a botulinum toxin containing implant.

16. A method for treating a bone tumor, the method comprising the step of locally administering botulinum toxin type A to a benign bone tumor, thereby causing a reduction in the size of the benign bone tumor, wherein the local administration is carried out by insertion of a botulinum toxin type A containing implant.

17. A method for treating a bone tumor, the method comprising the step of locally administering botulinum toxin type B to a benign bone tumor, thereby causing a reduction in the size of the benign bone tumor, wherein the local administration is carried out by insertion of a botulinum toxin type B containing implant.

* * * * *